(12) United States Patent
Alander et al.

(10) Patent No.: US 9,809,618 B2
(45) Date of Patent: Nov. 7, 2017

(54) ENRICHMENT OF TRITERPINE ESTERS (71) Applicant: AAK AB (PUBL), Malmö (SE)

(72) Inventors: Jari Alander, Danderyd (SE); Staffan Norberg, Karlshamn (SE); Krister Hed, Karlshamn (SE)

(73) Assignee: AAK AB, Malmo (SE)

( * ) Notice: Subject to any disclaimer, the term of this patent is extended or adjusted under 35 U.S.C. 154(b) by 0 days.

(21) Appl. No.: 15/026,014

(22) PCT Filed: Sep. 30, 2014

(86) PCT No.: PCT/SE2014/051134
§ 371 (c)(1),
(2) Date: Mar. 30, 2016

(87) PCT Pub. No.: WO2015/047187
PCT Pub. Date: Apr. 2, 2015

(65) Prior Publication Data
US 2016/0244480 A1    Aug. 25, 2016

(30) Foreign Application Priority Data

Sep. 30, 2013 (SE) ........................................ 1351145

(51) Int. Cl.
| C07J 53/00 | (2006.01) |
| C11C 3/10 | (2006.01) |
| A23D 9/007 | (2006.01) |
| C11B 3/02 | (2006.01) |
| C11B 3/10 | (2006.01) |
| C11B 3/12 | (2006.01) |
| C11C 1/08 | (2006.01) |
| C11C 3/06 | (2006.01) |

(52) U.S. Cl.
CPC ............ *C07J 53/002* (2013.01); *A23D 9/007* (2013.01); *C11B 3/02* (2013.01); *C11B 3/10* (2013.01); *C11B 3/12* (2013.01); *C11C 1/08* (2013.01); *C11C 3/06* (2013.01); *C11C 3/10* (2013.01)

(58) Field of Classification Search
CPC ........... C07J 53/002; C11C 3/10; C11C 3/003
See application file for complete search history.

(56) References Cited

U.S. PATENT DOCUMENTS

| 6,586,201 B1 * | 7/2003 | May ..................... B01D 15/325 |
| | | 210/606 |
| 2002/0058827 A1 | 5/2002 | Wollmann et al. |
| 2005/0016059 A1 | 1/2005 | Kovacs et al. |
| 2011/0220483 A1 | 9/2011 | Margnat et al. |

FOREIGN PATENT DOCUMENTS

| MY | EP 1394144 A1 * | 3/2004 |
| WO | WO 2009/113935 A1 | 9/2009 |

OTHER PUBLICATIONS

International Search Report and Written Opinion, PCT/SE2014/051134, dated Dec. 16, 2014.

* cited by examiner

*Primary Examiner* — Paula A Zucker
(74) *Attorney, Agent, or Firm* — Finnegan, Henderson, Farabow, Garrett & Dunner, LLP (57) ABSTRACT

A new process for enriching triterpene esters comprising: providing a mixture comprising a non-distilled vegetable oil and/or a non-distilled vegetable fat, further comprising triterpene esters, performing a mild transesterification with a lower alcohol, removing lower alcohol esters by deodorization, physical refining, evaporation or distillation, and recovering the remaining fraction rich in triterpene esters. Triterpene esters enriched with the method as well as uses of the same are also provided. One advantage is that it is a more economically viable way of achieving higher concentration of triterpene esters. There is both the chance to fully keep the natural distribution of triterpene esters but in the other end also to replace the natural level of cinnamic and acetic acids-triterpene esters with a high level of long fatty acid triterpene-esters.

29 Claims, 2 Drawing Sheets

ENRICHMENT OF TRITERPINE ESTERS

This application is a national stage filing under 35 U.S.C. §371 of International Application No. PCT/SE2014/051134 filed on Sep. 30, 2014, which claims the benefit of the filing date of Swedish Patent Application No. 1351145-6, filed Sep. 30, 2013, all of which are incorporated herein by reference.

TECHNICAL FIELD

The present invention relates generally to a process for enriching triterpene esters from sources comprising vegetable oils and fats, where the source material comprises an amount of triterpene esters.

BACKGROUND

Typical triterpenes are terpenes consisting of six isoprene units and typically have the molecular formula $C_{30}H_{48}$. Pentacyclic triterpenes can be classified into lupane, oleanane, or ursane groups. Animals, plants, and fungi, create triterpenes, like, squalene, ambrein and ganoderic acid.

Figure 2:
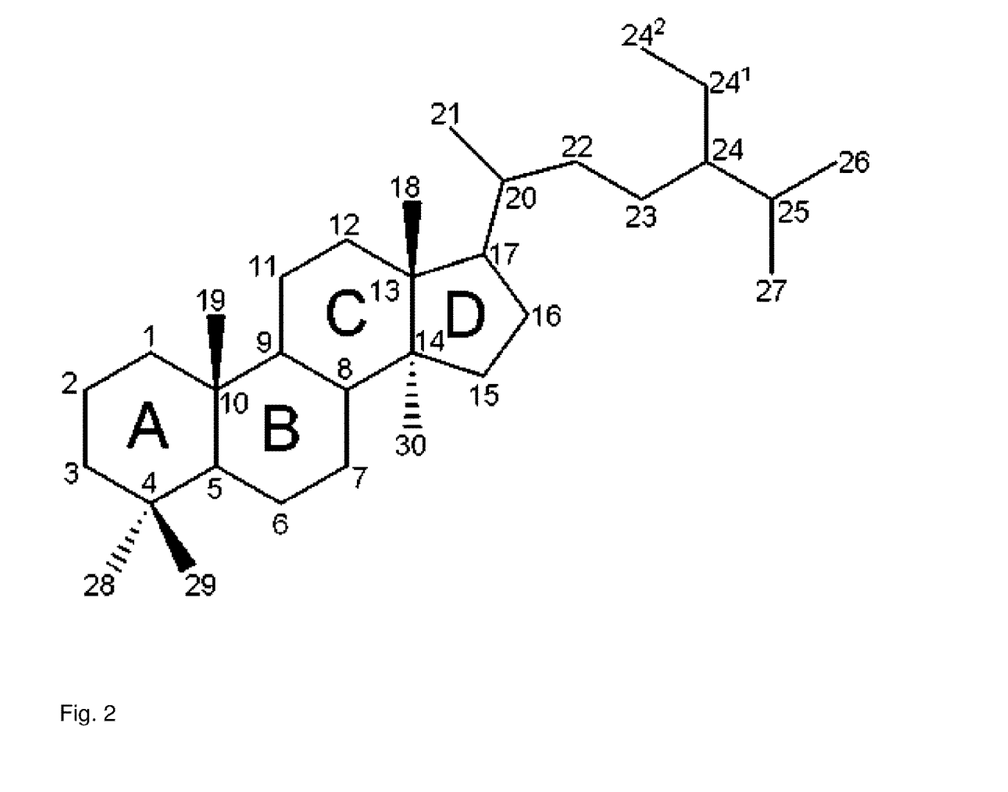
FIG. 2 shows the generic steroidal skeleton of a triterpene.

The steroidal skeleton depicted in FIG. 2 gives the generic structure for sterols and triterpenes. Most phytosterols (plant sterols) are tetracyclic, as in the picture. Many triterpenes can also be pentacyclic. There is generally an OH-group in position 3. This OH-group can be esterified or free, hence the differentiation between sterol esters and free sterols. The methyl groups in position 4 distinguish triterpenes from other steroidal compounds. Both methyl groups are present in triterpenes, one methyl group is present in methylsterols and no methyl groups are found in the desmethylsterols. The typical plant and animal sterols are desmethylsterols and these are colloquially known as phyto- and zoo-sterols. The most common phytosterol is beta-sitosterol. A huge variety of structures are known, defining different classes of triterpenoids. Pentacyclic structures usually have higher melting points compared to the tetracyclic steroids and are more difficult to isolate from the plant materials.

In shea butter, several classes of triterpenoids are known, including lupanes, ursanes and oleananes. Each of these classes can be represented by several individual triterpene alcohols. The triterpene alcohols in shea butter are usually esterified to cinnamic, acetic and other carboxylic acids.

There are today three main commercial routes to enrich unsaponifiable matter such as triterpene esters from vegetable oils; via molecular distillation, via solvent fractionation and via hydrolysation.

Fractionation is a method to separate materials based on the melting point, where for example, the high-melting triglycerides are made to crystallize, leaving the unsaponifiable matter dissolved in the liquid phase. Without hydrogenation the maximum concentration obtained is below 25 wt % of unsaponifiable content. Hydrogenation followed by interesterification and repeated fractionations can give a higher concentration unsaponifiable matter, up to 70 wt %. Hydrogenation and interesterification will lead to chemical modification of the unsaponifiable matter, for example changing the proportions of cinnamic, acetic and fatty acid esters of triterpene alcohols found in shea butter. The processes used are also very complex and using large capacity. At least for some productcategories the hydrogenation itself is less desirable from a consumer point of view.

Molecular distillation (also named short path distillation) is a method using extremely low pressure, in the order of magnitude around 0.001 Pa. The temperature in commercial units hardly goes above 260° C. The method uses the boiling point to separate different chemical species from each other. The limitations are that at lowest available pressure the boiling points must be lower than 260° C. for parts or the whole of the material and there must be a difference in boiling point between the molecules that are to be separated. In the case of shea butter, the triterpene acetates have the lowest boiling point, followed by diacylglycerides and almost at the same temperature, triterpene cinnamates, which makes it difficult to completely separate the acylglycerides from the triterpene esters.

Hydrolysation can be performed by adding alkali/water or water/high temperature to hydrolyse the ester bonds. Here also the triterpene ester bonds are also potentially broken, producing free triterpene alcohols with low solubility and high melting points.

WO 97/21697, U.S. Pat. No. 5,627,289, U.S. Pat. No. 4,451,564, U.S. Pat. No. 4,148,810 all disclose methods to produce concentrates of unsaponifiable matter where it is necessary to remove about 98% oil by distillation at about 220-260° C. and 3-20 mbar pressure. All those documents describe procedures where the starting material is a distillate from deacidification of vegetable oils. Thus the mixture used as a starting material has been subjected to distillation in the above disclosures, which does not preserve the natural composition of the triterpene esters. It also adds to the complexity and cost in the above disclosed processes.

US20110220483 discloses a process to produce sterol alcohols and triterpene alcohols from a distillate fraction. Enrichment of esters of triterpenes is not disclosed.

US20110220483 discloses that the ingoing material is in fact the distillation fraction when deodorising an oil. The process is a high temperature process, typically 200 to 250° C. under low pressure conditions, typically 1-50 mbar. Sparge steam is often used to enable all volatile products to be removed in the distillation phase. Here free sterols alcohols are distilled off with a number of other molecules such as free fatty acids, triglycerides, hydrocarbons, squalanes and impurities. Peroxides and aldehydes follow with the distillation phase. This is the starting material. In the distillation fraction very few triterpene esters are found as they are kept in the residual.

After that in order to enrich the alcohols of the sterols it has to go through a number of process steps, which all require very different design, such being able to handle both very low pressure and very high pressure, high temperatures and low temperatures. Except for the complex production method itself, the method will not result in native sterol esters, but alcohols of sterols and triterepenes without any acid bound to them. Free sterols and triterpene alcohols have a very much higher melting point than in the form of an ester, which make them difficult to use in a number of different applications.

US 20020058827 discloses using a distillation fraction as the starting material. More than 95% of the sterols in fact is in form of a sterol alcohol and less is in form of sterol ester. The distillate is then reacted with glycerol at a very high temperature, 215° C., which is not a gentle and energy efficient method.

In summary US 20020058827 and US20110220483 do not disclose a process where the main form of sterols are in the form of an ester, instead sterol alcohols are enriched. The ratio of sterol esters/sterol alcohol is less than 0.05.

In view of the above described drawbacks there is room for an improved method to enrich triterpene esters.

SUMMARY

It is an object of the present invention to obviate at least some of the disadvantages in the prior art and provide an improved method to enrich triterpene esters (TTP-esters) as well as to provide a mixture and uses of the enriched TTP-esters.

In a first aspect there is provided a process for enrichment of triterpene esters, the process comprising the steps: a) providing a mixture comprising at least one selected from the group consisting of a vegetable oil and a vegetable fat, said mixture further comprising triterpene esters, wherein vegetable oil and vegetable fat in the mixture has not been subjected to distillation b) performing a mild transesterification with at least one lower alcohol at a temperature equal to or lower than the boiling point of the mixture, to obtain lower alcohol esters, and c) removing lower alcohol esters by at least one selected from the group consisting of deodorisation, physical refining, evaporation and distillation, and recovering the remaining fraction rich in triterpene esters.

In a second aspect there is provided a mixture comprising triterpene esters, wherein the mixture comprises more than 85 wt % triterpene esters, and wherein the amount of diglycerides in the mixture is less than 1 wt %.

In a third aspect there is provided use of a triterpene ester enriched according to the process described above for at least one selected from the group consisting of, i) as a constituent in soft-shelled capsules, ii) as an additive in a cosmetic product, and iii) as an additive in a lotion.

Further embodiments are defined in the appended claims, which are specifically incorporated herein by reference.

Advantages include that there is provided a more economically viable way of achieving higher concentration of TTP esters with a natural distribution of TTP esters. There is both the possibility to fully keep the natural distribution of TTP esters but in the other end also to replace the natural level of cinnamic and acetic acids-TTP esters with a high level of long fatty acid TTP-esters, which have very different physical properties, which in turn make the TTP-esters easier to use in certain applications. Compared to processes where the starting material has been subjected to distillation, the present invention has the advantage that the natural composition of the triterpene ester is kept.

Compared to traditional fractionation, advantages include that high concentration TTP-ester concentration can be obtained without modifying the product by for instance hydrogenation. Also a higher content of TTP-ester, for instance above 80 wt %, can be obtained.

Advantages compared to molecular distillation include that the TTP-ester content can reach above 80 wt % while it is difficult to go above 65 wt % with ordinary molecular distillation. The natural mix of TTP esters is retained (ratio triterpene acetate/triterpene cinnamate is around 0.4) while molecular distillation will increase the concentration of triterpene acetate. Already at 50 wt % TTP ester content the ratio triterpene acetate/triterpene cinnamate is around 0.8 and when reaching 65 wt % of TTP ester content the ratio exceeds 1 and it can also reach close to 2 in some cases.

The process and product of this invention also offers improvement in the crystallization properties of the final product by exchanging long chain fatty acids for the acetic and cinnamic acid found in shea butter triterpene esters. Triterpene acetate easily crystallizes into a high melting solid (melting point 235° C.). Molecular distillation allows no separation of long chain fatty acid triterpene esters. The reason is that the boiling point becomes too high and too close to the boiling point of triglycerides.

In the molecular distillation process the molecules which are oxidized are enriched together with the TTP-esters while in the new process the oxidized components are removed as in normal distillation thereby increasing the oxidation stability.

A fluid and transparent/translucent appearance of the product can be obtained with the new method in contrast to the product obtained from molecular distillation. In molecular distillation the diacylglycerides existing in the starting material will also enrich with the TTP-esters. Diacylglycerides have higher melting points and will crystallize with time at room temperature which in the best case can give a white appearance but in many cases an inhomogeneous appearance of oil and white spots. The new route also allows addition of an oil or additive of choice, still keeping the TTP-level high.

Compared to products obtained by hydrolysation, the natural blend of TTP esters is kept while hydrolysis results in the formation of triterpene alcohols. The material obtained by the new process is easier to use in application due to the presence of the lower melting ester form. Hydrolysis results in a pure triterpene alcohol which crystallizes very rapidly to hard crystals with a melting point above 200° C. The new route allows the TTP-esters to remain in a liquid state which is easier to add into applications and also gives better bio-availability.

Compared to the prior art it is an advantage that there is only required one transesterification step. After that reaction the triterpene esters can be enriched. More than one reaction step is thus not necessary with the process disclosed herein.

BRIEF DESCRIPTION OF THE DRAWINGS

The invention is now described, by way of example, with reference to the accompanying drawings, in which.

DETAILED DESCRIPTION

Before the invention is disclosed and described in detail, it is to be understood that this invention is not limited to particular compounds, configurations, method or process steps, substrates, and materials disclosed herein as such compounds, configurations, method or process steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

As used herein, "%" or "percentage" all relates to weight percentage i.e. wt. % or wt.-% if nothing else is indicated. Ratios are calculated by weight unless nothing else is indicated.

If nothing else is defined, any terms and scientific terminology used herein are intended to have the meanings commonly understood by those of skill in the art to which this invention pertains.

As used herein the term "deodorisation" refers to heating a mixture and adding a gas such as steam, most often under a vacuum. A part of the mixture is in general removed during deodorising. The deodorising can include all or some of the following steps: deaeration, heating, deodorising/steam stripping, heat recovery/cooling, final cooling and polishing filtration. It is important to note that as used herein distillation is not encompassed within the term "deodorisation". Thus a mixture or a substance which is subjected to deodorisation is not considered to be distilled.

As used herein the term "interesterification" or "transesterification" in connection with a triterpene ester refers to the exchange of a part of the triterpene ester. An example includes exchange of the cinnamate in triterpene cinnamate for an organic molecule with a longer carbon chain.

As used herein the term "lower alcohol" is defined as an organic molecule with at least one OH group bound to a carbon atom, where the total number of carbon atoms in the alcohol is equal to or lower than 6. The alcohol can be linear, branched or cyclic.

As used herein the term "mild" in connection with transesterification or interesterification is defined in relation to the transesterification or interesterification temperature, in particular "mild" refers to a temperature which is lower than or equal to the boiling point of the mixture.

As used herein the term "peroxide value" is defined as the amount of peroxide oxygen per 1 kilogram of fat or oil. If nothing else is indicated this is expressed in units of milliequivalents $O_2$ per kg. 1 milliequivalents=0.5 millimole; because 1 mEq of $O_2$=1 mmol/2=0.5 mmol of $O_2$, where 2 is valence.

As used herein the term "physical refining" refers to use of differences in physical properties to separate a mixture of compounds. Such differences include differences in boiling point. Deodorisation is one such physical refining.

As used herein the term "vegetable" is interpreted broadly so that it encompasses all plants of the kingdom Plantae.

As used herein the term "vegetable fat" refers to triglycerides of vegetable origin which are solid at normal room temperature 20° C.

As used herein the term "vegetable oil" refers to triglycerides of vegetable origin which are liquid at normal room temperature 20° C.

It is understood that a vegetable fat and a vegetable oil is made of some plant or part thereof and thus it comprises a number of further substances such as lipids including fats, waxes, sterols, fat-soluble vitamins, monoglycerides, diglycerides, triglycerides, phospholipids, hydrocarbons and other organic substances. Such organic substances include but are not limited to triterpene esters. Further other organic molecules can be present including but not limited to carbohydrates, proteins, RNA, and DNA.

In a first aspect there is provided a process for enrichment of triterpene esters, the process comprising the steps: a) providing a mixture comprising at least one selected from the group consisting of a vegetable oil and a vegetable fat, said mixture further comprising triterpene esters, wherein vegetable oil and vegetable fat in the mixture has not been subjected to distillation b) performing a mild transesterification with at least one lower alcohol at a temperature equal to or lower than the boiling point of the mixture, to obtain lower alcohol esters, and c) removing lower alcohol esters by at least one selected from the group consisting of deodorisation, physical refining, evaporation and distillation, and recovering the remaining fraction rich in triterpene esters.

The reactants are mixed and reacted and after the mild transesterification in step b) the separation in step c) is carried out. Regarding step c) it is an important feature that the lower alcohol esters are removed and the desired triterpene esters remain in the mixture. Optionally the removed lower alcohol esters can be recovered and utilized for other purposes. What remains after the lower alcohol esters have been removed comprises a high amount of triterpene esters. The remaining, i.e. the phase with higher boiling point is recovered in step c). The compounds with lower boiling point are removed, including the lower alcohol esters.

Even if it is described that the lower alcohol esters are removed it is understood that small amounts may still be present after such a removal. It is also understood that if it is described that the triterpene esters remain in the mixture and are not removed, small amounts of triterpene esters may anyway be removed during such a separation step due to imperfections in the process.

The source of the mixture in step a) can vary. The mixture is made of some plant or part thereof and comprises vegetable oil and/or vegetable fat together with at least one triterpene ester. In one embodiment the mixture comprises at least one vegetable oil. In one embodiment the mixture comprises at least one selected from the group consisting of rice bran oil, shea butter, shea butter oil, avocado oil, olive oil, soybean oil, rapeseed oil, mango butter, argan oil, palm oil, red palm oil, coconut oil, palm kernel oil, safflower oil, cocoa butter, almond oil, sunflower oil, peach kernel oil, evening primrose oil, sesame oil, illipe butter, borage oil, cottonseed oil, babassu oil, sal butter, kokum butter, shorea butter, corn oil, corn fiber oil, groundnut oil, flax seed oil, murumuru butter, cupuacu butter, and macadamia oil. In another embodiment the mixture comprises at least one selected from the group consisting of rice bran oil, shea butter, shea butter oil, and corn fiber oil. In yet another embodiment the mixture comprises shea butter.

In one embodiment the mixture used as starting material is a crude oil and/or fat. In an alternative embodiment the mixture used as a starting material is a refined oil and/or fat and in yet another embodiment it is a mixture of a crude and refined oil and/or fat. The mixture used as a starting material has not been subjected to distillation. The mixture used as starting material can also be a refined vegetable oil and/or vegetable fat, where the refinement does not include distillation. The mixture used as starting material is non-destilled, i.e. the mixture comprising vegetable oil and/or the vegetable fat and further comprising triterpene esters has not been subjected to distillation, hence the term non-destilled.

It is understood that the vegetable oil and vegetable fat in the starting mixture has not been subjected to distillation. It is then implicit that the triterpenes ester(s) mixed with the vegetable fat and/or vegetable oil is also not subjected to distillation before starting the process. In an alternative embodiment more than 90 wt %, preferably more than 95 wt % of the vegetable oil and vegetable fat in the starting mixture has not been subjected to distillation. A skilled person realizes that some drawbacks will occur in an increasing degree the more oil/fat subjected to distillation is added. Thus it is preferred to keep this fraction as low as possible and most preferred not to have distilled oil/fat at all.

It is understood that the vegetable oil and/or the vegetable fat further comprises the triterpenes esters to be enriched. Thus the mixture comprising at least one selected from a vegetable oil and a vegetable fat also comprises triterpenes esters. By the term triterpenes esters at least one type of triterpene ester is envisaged.

The feature of not starting with distilled oil and/or fat has the advantage that the natural composition of the triterpene esters are kept. For instance the triterpene esters themselves do not essentially or do not at all participate in any chemical reactions that would change the natural composition of the triterpene esters.

US20110220483 discloses a process to produce sterol alcohols and triterpene alcohols from a distillate fraction. This is in contrast to the present invention which is a method to enrich esters of triterpenes. Sterol alcohols and triterpene alcohols have a higher melting point and different surface activity vs triterpene esters. Thus the ester form is sought for when the formulator are seeking for a easy to apply ingredient.

Before the mild transesterification in step b) the mixture can be treated to further purify and/or improve and/or modify it. In one embodiment the mixture is subjected to at least one selected from the group consisting of refining, degumming, neutralization, bleaching, and deodorisation before step b). In one embodiment the mixture is subjected to solvent fractionation before step b). In another embodiment the mixture is subjected to hydrogenation before step b). In yet another embodiment the mixture is subjected to a combination of the processes detailed above before applying step b).

In one embodiment the triterpene esters in the mixture are subjected to interesterification before step b). This will alter the properties of the triterpene esters and thus provides a possibility to modify the triterpene esters to better suit the desired application. One example is the exchange of triterpene cinnamate ester with another ester with a longer fatty acid. Alternatively the interesterification step is omitted and then the present process has the advantage that it preserves the natural ratio between different triterpene esters.

In one embodiment the triterpene esters in the mixture are subjected to at least one selected from the group consisting of partial hydrogenation and full hydrogenation before step b).

In one embodiment the mild transesterification in step b) is performed with a lower alcohol wherein the lower alcohol comprises 1-6 carbon atoms. In an alternative embodiment the mild transesterification in step b) is performed with a lower alcohol wherein the lower alcohol comprises 1-5 carbon atoms. In another embodiment the mild transesterification in step b) is performed with a lower alcohol selected from the group consisting of methanol, ethanol, propanol, isopropanol, butanol, isobutanol, isoamyl alcohol and pentanol. In yet another embodiment the mild transesterification in step b) is performed with at least one selected from the group consisting of ethanol and isopropanol as the lower alcohol. In a further embodiment the mild transesterification in step b) is performed with a mixture of methanol and ethanol as lower alcohols. In one embodiment the mild transesterification in step b) is performed with ethanol as the lower alcohol.

In one embodiment the lower alcohol does not comprise more than 0.5 wt % water. It is an advantage that the water content in the alcohol is kept low so that the transesterification reaction proceeds further towards the product. One advantage of using a mixture of methanol and ethanol is that the water absorption ability of methanol is low so that the mixture is less prone to absorb water compared to pure ethanol. In one embodiment the mild transesterification in step b) is performed with methanol and at least one other lower alcohol.

In one embodiment the mild transesterification in step b) is performed with at least one catalyst. In one embodiment the mild transesterification in step b) is catalysed by an acid catalyst. In an alternative embodiment the mild transesterification in step b) is catalysed by a base catalyst. In one embodiment the mild transesterification in step b) is catalysed by at least one selected from the group consisting of $NaOCH_3$, $NaOCH_2CH_3$, NaOH, and KOH. In yet an alternative embodiment the mild transesterification in step b) is catalyzed by an enzyme.

The preferred low water content applies to transesterification which are not catalyzed by enzymes. During enzymatic catalysis higher water content can be accepted, and for some enzymes a certain water content is even required. A skilled person can in the light of this description adapt the water content to the type of catalysis which is applied, for instance if an enzyme is used the skilled person is able to select a water content which is normally used and recommended for that particular type of enzyme.

Advantages of using an enzyme include that the temperature is kept lower which is more gentle. Further the energy consumption is lower due to less requirements for heating.

In one embodiment the mild transesterification in step b) is performed at a temperature from 5° C. below the boiling point of the mixture to the boiling point of the mixture. In one embodiment the mild transesterification in step b) is performed at a temperature not higher than 90° C. In one embodiment the mild transesterification in step b) is performed at a temperature from about 60 to about 78° C. The upper limit 78° C. is suitable when ethanol is used as a lower alcohol with regard to the boiling point of the mixture. It is an advantage compared to the prior art that the temperature in step b) can be kept low.

The mild transesterification in step b) should be carried out at or below the boiling point of the mixture, measured at the relevant pressure at which the reaction is carried out. It is an advantage if the transesterification is not carried out too much below the boiling point, since then the reaction can be made quicker and more efficient. Thus the temperature is suitably selected in the interval with the upper limit being the boiling point of the mixture at the relevant pressure and the lower limit is 5° C. below that boiling point. In an alternative embodiment the lower limit is instead 10° C. below the boiling point.

In one embodiment the mild transesterification in step b) is performed at atmospheric pressure.

In one embodiment the mild transesterification in step b) is performed during a reaction time from about 15 minutes (min) to about 15 hours (h), such as about 15 min, 30 min, 1 h, 2 h, 3 h, 4 h, 5 h, 6 h, 7 h, 8 h, 9 h, 10 h, 11 h, 12 h, 13 h, 14 h, 15 h. In one embodiment the mild transesterification is performed in 60 minutes or less. In some further embodiments, the mild transesterification in step b) is performed during a reaction time from about 15 minutes to about 60 minutes. It is an advantage that the process can be performed with a relatively short mild transesterificaiton during less than 60 minutes.

In one embodiment a second mixture comprising at least one selected from the group consisting of a vegetable oil and a vegetable fat is added after step b) before step c). It is understood that such a second mixture may comprise further substances in addition to vegetable oil and/or vegetable fat. Such additional substances are the same as detailed above for the mixture provided in step a). The addition of a second mixture comprising a vegetable oil and/or a vegetable fat after step b) but before step c) has the advantage that the physical properties of the final mixture improves, in particular the viscosity decreases and the resulting mixture becomes considerable easier to handle. In one embodiment the same at least one selected from the group consisting of vegetable oil and vegetable fat as in step a) is added after step b) before step c), i.e. the same mixture as provided in step a) is added again after step b before step c). If the same mixture as in step a) is utilized for the addition after step b) before step c) this has the advantage that only one type of raw material has to be supplied to the process. That simplifies the process in an industrial scale. It is also possible to achieve the benefits of an addition with another source of vegetable oil and/or vegetable fat.

In one embodiment step c) is carried out at a temperature from 140 to 250° C. In one embodiment step c) is first carried out at a temperature from 140 to 190° C. and after a while at a temperature from 200 to 250° C. In an alternative embodiment step c) is carried out at an increasing temperature starting from a temperature in the interval 140-190° C. and gradually increasing the temperature to a temperature in the interval 200-250° C. The stepwise and gradual increase in temperature has the advantage that compounds are removed gradually from the mixture depending on their boiling point. If the temperature would be increased to the highest temperature at once, the result could be an undesired and too quick removal of the compounds to be removed.

In one embodiment step c) is carried out at a pressure from 1 to 30 mbar. In an alternative embodiment step c) is carried out at a pressure from 1 to 5 mbar.

In one embodiment step c) is carried out with addition of steam. The deodorisation in step c), if used is carried out with an additional gas or gas mixture, which in one embodiment is steam.

In one embodiment the amount of remaining triterpene esters after step c) is more than 85 wt %. It is an advantage of the process that it easily allows a high content of triterpene esters to be reached at a reasonable cost.

In one embodiment the ratio calculated by weight of triterpene esters/triterpenes alcohols in the end product is above 1. It is an advantage with a higher ratio, since the product is easier to use if there is less alcohol in it. Triterpene alcohols have low solubility and high melting points and are thus less preferred for many applications. Further both free sterols and triterpene alcohols have a much higher melting point than in the form of an ester, which make them difficult to use in a number of different applications. Thus a skilled person realizes that if there is less triterpenes alcohols in the end product it is a more preferred product. In an alternative embodiment the ratio calculated by weight of triterpene esters/triterpenes alcohols in the end product is above 2. In yet another embodiment the ratio calculated by weight of triterpene esters/triterpenes alcohols in the end product is above 4. In another embodiment the ratio calculated by weight of triterpene esters/triterpenes alcohols in the end product is above 6. In another embodiment the ratio calculated by weight of triterpene esters/triterpenes alcohols in the end product is above 8. In another embodiment the ratio calculated by weight of triterpene esters/triterpenes alcohols in the end product is above 10. It is considered that the end product remains after step c, when the lower alcohol esters have been removed. The remaining fraction is rich in triterpenes esters and is recovered. The above ratio applies to this remaining fraction which is recovered.

In one embodiment the peroxide value of the mixture after step c) is less than 1 milliequivalents/kg. This applies to the mixture directly after the process. When the resulting mixture has been stored for a while this value may increase. It is an advantage that the process gives a product with a low peroxide value.

In a second aspect there is provided a mixture comprising triterpene esters, wherein the mixture comprises more than 85 wt % triterpene esters, and wherein the amount of diglycerides in the mixture is less than 1 wt %.

In one embodiment of the second aspect the peroxide value of the mixture is less than 10 milliequivalents/kg. In an alternative embodiment the peroxide value of the mixture is less than 1 milliequivalents/kg. In yet another alternative embodiment the peroxide value of the mixture is less than 0.2 milliequivalents/kg.

In one embodiment of the second aspect the ratio (tc/ta) between triterpene cinnamates (tc) and triterpene acetates (ta) in the mixture is from 1.5 to 3. A ratio in this interval can be obtained by using shea butter and/or shea butter oil as raw material in step a) in the process.

In a third aspect there is provided use of a triterpene ester enriched according to the process described above for at least one selected from the group consisting of, i) as a constituent in soft-shelled capsules, ii) as an additive in a cosmetic product, iii) as an additive in a lotion, iv) as an additive in ointments, lip care and colour cosmetics, v) as an additive in OTC lotions or OTC ointments. OTC means "Over-The-Counter".

Figure 1:
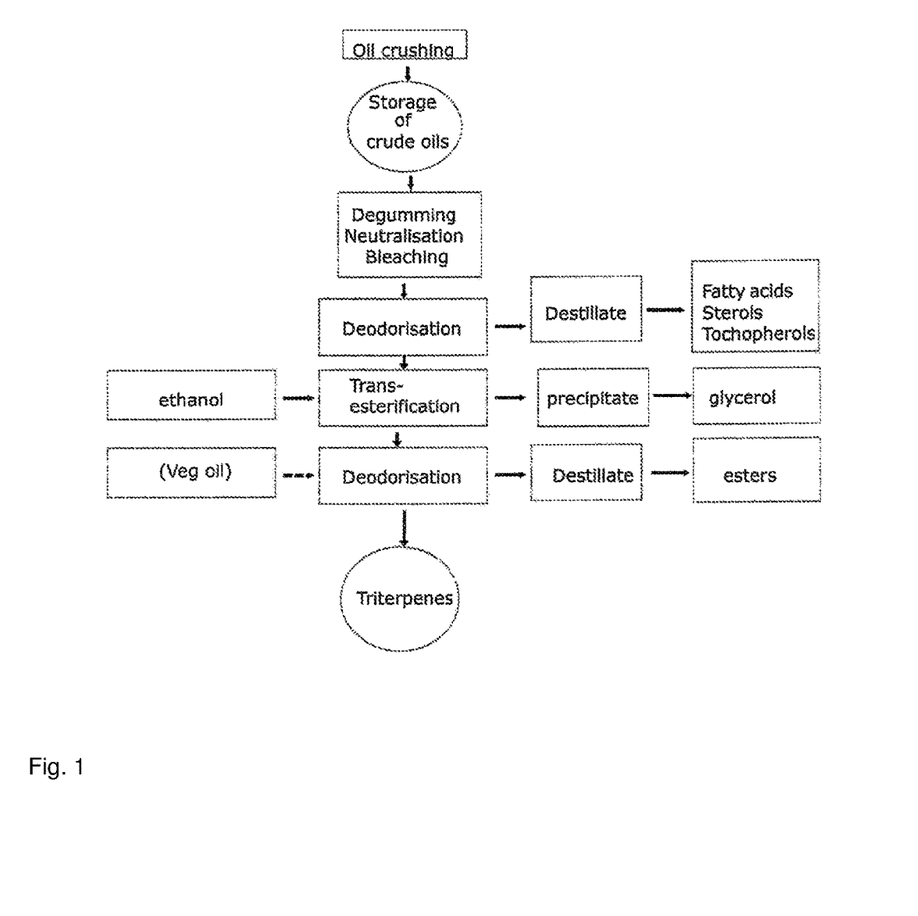
FIG. 1 shows a flow chart detailing one embodiment according to the invention.

One embodiment of the invention is detailed in FIG. 1. After recovering oils from a plant the oils are stored in a storage tank. The oil is subjected to degumming, neutralization and bleaching. Subsequently there is a step (deodorisation) to remove certain components of the oil including fatty acids, sterols and tochopherols. These substances can be recovered. Then the transesterification is performed under mild conditions with added ethanol. During the transesterificaiton the precipitate (glycerol) does not have to be discarded but can also be recovered in order to improve the overall economy of the process. After the mild transesterification a deodorisation is performed with added vegetable oil. The compounds with higher boiling point are removed and can also be recovered for improved economy. The desired triterpene esters essentially remain in the mixture and are recovered.

Other features and uses of the invention and their associated advantages will be evident to a person skilled in the art upon reading the description and the examples.

It is to be understood that this invention is not limited to the particular embodiments shown here. The embodiments are provided for illustrative purposes and are not intended to limit the scope of the invention since the scope of the present invention is limited only by the appended claims and equivalents thereof.

EXAMPLES

As starting material four batches of shea butter oil during 2012 were analyzed with respect to TTP ester content.

|  | May 2012 | June 2012 | September 2012 | November 2012 |
| --- | --- | --- | --- | --- |
| Triterpenacetate | 3.0 | 2.8 | 2.8 | 2.8 |
| Triterpencinnamate | 6.4 | 6.5 | 6.4 | 6.4 |
| Fatty acid triterpenester | 0.9 | 1.2 | 1.2 | 1.0 |
| Triterpenester total | 10.3 | 10.5 | 10.4 | 10.1 |

In shea butter oil the typical level of TTP esters are around 10 wt %, of which the majority of the esters are esterified with either acetate or cinnamate. The normal ratio cinnamate/acetate is around 2:1. Shea butter oil is characterized by being a liquid fraction of shea butter which at room temperature can appear clear or hazy.

Shea butter is characterized by having a melting point between 30 to 45° C. However by modifying shea or shea butter oil by for instance hydrogenation or interesterification higher melting points, up to 65° C. can be achieved.

The process is divided into two steps. The first step is the production of an ester with a low boiling point. The second part is the separation of the ester and the unsaponifiable part.

Experiment 1: The Making of an Shea Butter Ethyl Ester

The raw material used were:
Shea butter oil characterized by being liquid at room temperature and with a TTP ester content of 10 wt %.
Ethanol containing 99.5 wt % ethanol originating from sugar cane.
The catalyst was NaOMe (NaOCH$_3$).
Citric acid:
Citric acid was used to neutralise the catalysts and/or the soap created by the catalysts to terminate the reaction.

1000 g of Shea butter oil, refined, bleached and deodorized according to standard procedure, was blended with ethanol (250 g). 7 gram of the catalyst was added and the mixture was heated at 1 atm and stirring. The temperature was kept at 65° C. for 30 minutes in order for the reaction to reach steady state. After the 30 minutes reaction time the stirring was stopped to allow the glycerol to separate at the bottom. After 30 minutes of separation two phases were seen, an upper phase (the ester phase) and a lower phase (glycerol phase). The glycerol phase was removed and weighed (87 g). Another 2 grams of catalyst was added to the remaining phase under stirring and the temperature increased to 75° C. and then kept at 75° C. for 30 minutes, and 1 atm. The mixture was stirred once again to reach steady state and to reach a low monoglyceride content (target below 1 wt %). The stirring was turned off to allow a glycerol phase to appear. The glycerol phase was once again removed (7 g). The ester was washed with water to stop reaction and remove traces of soap and then dried. The excess of ethanol was removed during the drying process. The yield of ester was 90% of the theoretical value. The final product was characterized by analyzing the content of three classes of molecules: monoglycerides, fatty acid ethyl esters and triterpene (TTP) esters.

The mono glyceride content was less than 1 wt %, the TTP ester content was 9 wt % and the fatty acid ethyl ester content was 89 wt %.

Experiment 2: Enriching TTP Ester 350 gram of the ester in experiment 1 was deodorized (190° C., 2 mbar, 20 g/h steam) for 30 minutes. The fatty acid ethyl esters were evaporated and condensed. The material remaining after removal of the ethyl esters, the deodorizer residue, 32 gram, was analyzed.

The residue contained 79% of unsaponifiable matter in form of triterpene esters and 21 wt % acylglycerides. Three classes of triterpene esters were found and identified as 20 wt % triterpene acetates, 51 wt % of triterpene cinnamates and 8 wt % of long chain fatty acid triterpene esters.

The product was very sticky and highly viscous, and thus difficult to handle.

Experiment 3: Enriching TTP-Ester Fraction with Shea Butter Oil 400 grams of ethyl esters from experiment 1 were blended with 20 grams of Shea butter oil and deodorized at 190° C., 2 mbar, 20 g/h steam. The deodorizer residue this time had lower viscosity and was clear. The yield of the residue was 61 grams. The total TTP ester content was 50 wt %.

Experiment 4: Transesterification of Shea Butter Triterpene Esters

The raw material used were:
Shea butter oil characterized by being liquid at room temperature and with an unsaponifiable matter content of 7 wt %.
Ethanol containing 99.5 wt % ethanol originating from sugar cane.
The catalyst was NaOMe.
Citric acid:
Citric acid was used to neutralise the catalysts and/or the soap created by the catalysts to terminate the reaction.

1000 g of Shea butter oil, refined, bleached and deodorized according to standard procedure, was blended with ethanol (250 g). 7 gram of the catalyst was added and the mixture was heated at 1 atm with stirring. The temperature was kept at 74° C. for 12 hours in order to let the triterpene cinnamates and acetates react and equilibrate. After the 12 hours reaction time the stirring was stopped to allow the glycerol to separate at the bottom. After 30 minutes of separation two phases were seen, an upper phase (the ester phase) and a lower phase (glycerol phase). The glycerol phase was removed and weighed (90 g). Another 2 grams of catalysts were added to the remaining phase under stirring and the temperature increased to 75° C. and then kept at 75° C. for 30 minutes and 1 atm. The mixture was stirred once again to reach steady state and to reach a low monoglyceride content (below 1 wt %). The stirring was shut off to allow a glycerol phase to separate. The glycerol phase was once again removed (20 g). The ester was washed with water to stop the reaction and to remove traces of soap and then dried. The excess of ethanol was removed during the drying process. The yield was 93% of the theoretical value. The final product was characterized by comprising of three classes of molecules, monoglycerides, fatty acid ethyl esters and triterpene esters.

The monoglyceride content was less than 1 wt %, the TTP ester content was 9 wt % and the fatty acid ethyl ester content was 89 wt %.

Experiment 5: Enriching Fatty Acid TTP-Esters 400 grams of esters from experiment 4 were blended with 16 grams of shea butter oil and deodorized at 190° C., 2 mbar, 20 g/h steam. The deodorizer residue remaining this time had low viscosity and was clear. The yield of the residue was 51 grams. The unsaponifiable matter content was 65 wt %. The long fatty acid TTP-esters content was increased to 11 wt % (Table 3). One month later it was still a clear liquid at room temperature.

Experiment 6: The Making of an Shea Butter Ethyl Ester from Solid Shea Butter The raw material used were:
Shea butter characterized by being solid at room temperature and with an unsaponifiable matter of 6 wt %.
Ethanol containing 99.5 wt % ethanol originating from sugar cane.
The catalyst was NaOMe.
Citric acid:
Citric acid was used to neutralise the catalysts and/or the soap created by the catalysts to terminate the reaction.

The shea butter was refined, bleached and deodorized according to standard procedure. 1000 g was mixed with ethanol (250 g) and 7 gram of the catalyst was added. and the mixture was heated at 1 atm and stirring. The temperature was kept at 74° C. for 30 minutes to allow the reaction to reach steady state. After 30 minutes of reaction time the stirring was stopped to allow the glycerol to separate at the bottom. After 120 minutes of separation two phases were seen, an upper phase (the ester phase) and a lower phase (glycerol phase). The glycerol phase was removed and weighed (81 g). Another 2 grams of catalyst was added to the remaining ester phase under stirring and the temperature increased to 75° C. and then kept at 75° C. for 30 minutes and 1 atm. The mixture was stirred once again to reach steady state and to reach a low monoglyceride content (below 1 wt %). The stirring was shut off to allow a glycerol phase to appear. The glycerol phase was once again removed (5 g). The ester phase was washed with water to stop reaction and remove traces of soap and then dried. The excess of ethanol was removed during the drying process. The yield was 78% of the theoretical, due to emulsion formation during the work-up. The final product was characterized by comprising three classes of molecules, monoglycerides, fatty acid ethyl esters and TTP esters.

The monoglyceride content was less than 2 wt %, the TTP esters content was 6 wt % and the ethyl ester content was 92 wt %.

Experiment 7: Enriching TTP-Ester with Shea Butter 400 grams of esters from experiment 6 was blended with 16 grams of shea butter and deodorized at 190° C., 2 mbar, 20 g/h steam. The residue this time had low viscosity and was clear. One day later it had solidified at room temperature. The yield of the residue was 7 wt %. The unsaponifiable matter content was 50 wt %.

Experiment 8: The Making of an Ethyl Ester from Rice Bran Oil

The raw material used were:
Rice bran oil with an iodine value of 95, characterized by being liquid at room temperature and with an unsaponifiable matter content of 4%. The unsaponifiable matter composition comprises mainly phytosterols, other sterols, triterpene alcohols (oryzanol) and squalene.
Ethanol containing 99.5% ethanol originating from sugar cane.
The catalyst was NaOMe.
Citric acid:
Citric acid was used to neutralise the catalysts and/or the soap created by the catalysts to terminate the reaction.
The rice bran oil was refined, bleached and deodorized according to standard procedure. 1000 g was mixed with ethanol (250 g) and 7 gram of the catalyst was added, the mixture heated at 1 atm and stirring to 74° C. The temperature was kept at 74° C. for 30 minutes to allow the reaction to reach steady state. After 30 minutes of reaction time the stirring was stopped to allow the glycerol to separate at the bottom. After 30 minutes of separation two phases were seen, an upper phase (the ester phase) and a lower phase (glycerol phase). The glycerol phase was removed and weighed (94 g). Another 2 grams of catalyst was added to the remaining ester phase under stirring and the temperature increased to 75° C. and then kept at 75° C. for 30 minutes, 1 atm. The mixture was once again stirred reach steady state and to reach a low monoglyceride content (below 1 wt %). The stirring was shut off to allow a glycerol phase to appear. The glycerol phase was once again removed (9 g). The ester was washed with water (containing citric acid 1 wt %) to stop reaction and to remove traces of soap and then dried. The excess of ethanol was removed during the drying process. The yield was 95% of the theoretical. The final product was characterized by containing three classes of molecules, monoglycerides, fatty acid ethyl esters and unsaponifiables.

The monoglyceride content was less than 1 wt %, the unsaponifiable content was 4 wt % and the ethyl ester content was 95 wt %.

Experiment 9: Enriching Rice Bran Unsaponfiables 400 grams of esters from experiment 8 was blended with 12 grams of rice bran oil and deodorized at 190° C., 2 mbar, 20 g/h steam. The yield of the residue was 29 grams. The unsaponifiable content was 49 wt %.

Experiment 10: Pretreating the Oil in Order to Increase the Long Fatty Acid Esters of Triterpene Esters 1000 grams of refined shea butter oil were dried at 90° C., 30 mbar, 60 minutes. Then nitrogen was used to restore the pressure to normal and 2 grams of catalyst (Sodium methylate from Degussa) were added and mixed. The pressure was reduced to 3 mbar and the temperature was kept at 90° C. with the blender going at 600 rpm. After 60 minutes another 2 grams were added and finally after 120 minutes another 2 grams of catalyst were added and kept with stirring for another 60 minutes and the citric acid were added to end the reaction.

To the sample, bleaching earth was added and allowed in the reactor for 30 minutes. The product were then filtered through a Millipore filter (5 μm) and deodorized at 190° C., 2 mbar, 20 g/h steam. The filtrate this time was clear. The yield of the filtrate was 942 grams. The unsaponifiable content was 12 wt %.

Experiment 11: Producing of an Ester

Shea oil from Experiment 10 was used
Ethanol containing 99.5% ethanol originating from sugar cane.
The catalyst was NaOMe.
Citric acid:
Citric acid was used to neutralise the catalysts and/or the soap created by the catalysts to terminate the reaction.
900 g of the shea oil from Experiment 10, was mixed with ethanol (285 g) and 8 gram of the catalyst. The mixture was heated at 1 atm and stirring until the temperature reached 75° C. The temperature was kept at 75° C. for 30 minutes in order for the reaction to reach steady state. After the 30 minutes reaction time the stirring was stopped to allow the glycerol to separate at the bottom. After 45 minutes of separation two clear phases were seen, the upper phase (the ester phase) and a lower phase (glycerol phase). The glycerol phase was removed and weighed (90 g). The ester was washed with water to stop reaction and remove traces of soap and then dried. The excess of ethanol was removed during the drying process. The yield was 93% of the theoretical. The day after the product was bleached. The final product was characterized by containing three classes of molecules, monoglycerides, fatty acid ethyl esters and TTP esters.

The monoglyceride content was just above 1 wt %, the TTP ester content was 12 wt % and the ethyl ester content was 87 wt %.

Experiment 12: Enriching Shea TTP-Fatty Acid Esters 500 gram of the ester in experiment 11 was deodorized (190° C., 2 mbar, 20 g/h steam) for 40 minutes. The fatty acid ethyl ester was evaporated and condensed. The deodorizer residue, (49 grams) was analysed.

The residue contained 86 wt % of TTP esters, comprising 4 wt % triterpene acetates, 11 wt % triterpene cinnamates and 71 wt % of triterpene esters of long chain fatty acids. The product has high viscosity.

Summary of Experiments 1-12

TABLE 1

| | Experiment | | | | |
|---|---|---|---|---|---|
| | 1 | 4 | 6 | 8 | 10 |
| oil type | Shea butter oil | Shea butter oil | shea butter | rice bran oil | Pretreated shea butter oil |
| Unsaponifiables before interesterification [wt %] | 10 | 7 | 6 | 4 | 12 |
| Unsaponifiables after insteresterification [wt %] | 10 | 9 | 6 | 4 | 12 |
| Yield (as of theoretcial yield) after washing and drying. [wt %] | 90 | 92 | 78 | 95 | 93 |

TABLE 2

| | Experiment | | | | | |
|---|---|---|---|---|---|---|
| | 2 | 3 | 5 | 7 | 9 | 12 |
| added oil | no | 5 wt % | 4 wt % | 4 wt % | 4 wt % | 0 |
| Yield [wt %] | 9 | 15 | 13 | 8 | 5 | 10 |
| Unsaponifiable matter [wt %] | 79 | 52 | 52 | 52 | 53 | 86 |

Some unsaponifiable matter compositions were further explored to identify the type of TTP-esters.

The following table summarizes the content expressed in wt % of certain substances in the products from different experiments.

TABLE 3

| | TTP-acetate (wt %) | TTP-cinnamate (wt %) | TTP-Fatty acid ester (wt %) | Total TTP (wt %) |
|---|---|---|---|---|
| Typical concentration in shea olein. | 2.8 | 6 | 1 | 9.8 |
| Experiment 2 | 19.8 | 50.9 | 7.6 | 78.5 |
| Experiment 3 | 15.8 | 31.8 | 4.8 | 52.4 |
| Experiment 5 | 25.0 | 28.9 | 11.1 | 65.0 |
| Experiment 11 | 0.7 | 1.7 | 10.1 | 12.5 |
| Experiment 12 | 4.1 | 10.7 | 71.1 | 85.9 |

Experiment 13 the Making of an Ethyl Sheate Ester from Crude Shea Butter Oil The raw material used were:

Crude Shea butter oil characterized by being liquid and with an TTP ester matter of 10 wt % and a free fatty acid level of 3 wt %.

Ethanol containing 99.5 wt % ethanol originating from sugar cane.

The catalyst was Lypozyme 435 from Novozymes.NaOH: 0.25 grams of NaOH was added to 10 kg of crude shea butter oil and allowed to stabilize over night "neutralized crude shea butter oil".

The neutralized crude Shea butter oil 500 g was blended with the catalyst 25 grams and at 1 atm, 45° C. for one hour with gentle stirring. Ethanol (20 g) was then added and allowed to react at 45° C., 1 atm with gentle stirring for one hour when more ethanol was added (20 g). The reaction continued in the same manner and ethanol was added every hour another 4 times, eg in total 120 grams of ethanol was added. After this the reaction was allowed to continue for another 18 hours at 45° C., 1 atm and with gentle stirring. The stirring was then stopped and after one hour two phases were formed. The lower, mainly containing the glycerol was removed. The stirring was started and more ethanol (20 g) was added. The temperature remained 45° C. and pressure was still 1 atm. Another 100 g of ethanol was added in portions of 20 g with one hour in between. After the last ethanol was added the reaction was allowed to continue for another 15 hours. The stirring was stopped and more glycerol phase appeared in the bottom of the reactor and removed. The ester was washed with water and then dried. The excess of ethanol was removed during the drying process. The theoretical yield would be 515 gram, but 480 grams were collected. The final product was characterized by containing of three classes of molecules, monoglycerides, ethanol fatty acid esters and TTP ester content.

The monoglyceride content was less than 1 wt %, the TTP ester content was 9 wt % and the ester content was 89 wt %.

Experiment 14: Enriching Fatty Acid TTP-Esters in Shea Butter Oil from Crude Shea Butter Oil 400 grams of esters from experiment 13 were blended with 14 grams of shea butter oil and deodorized at 190° C., 2 mbar, 20 g/h steam. The remaining phase was quite sticky. The yield of the remaining was 50 grams. The unsaponifiable content was 69 wt %.

Methods of Analysis:

Analysis of Ester:

The ester was analysed with a GC method, where esters, monoglycerides, di-glycerides and tri-glycerides were analysed. The unsaponifiables and diglycerides co-eluted, but since the triglyceride content always was close to zero and the monoglyceride content was below 1 wt % in all samples except one, the diacylglycerides were considered to be close to zero.

The Analysis of the Enriched Phase:
Iodine values:
The iodine value is measured via the method called Hanus.
Unsaponifiable Matter:
The unsaponifiable matter content was measured by NIR which was calibrated vs a standard wet chemical method.
Triterpene ester analysis for shea:
The exact type and level of TTP-esters were analysed by a GC-MS method.

The invention claimed is:

1. A process for enriching triterpene esters comprising:
providing a mixture comprising at least one non-distilled vegetable oil or non-distilled vegetable fat, wherein the mixture further comprises at least one triterpene ester,
performing a mild transesterification with at least one lower alcohol at a temperature equal to or lower than the boiling point of the mixture, to obtain lower alcohol esters,
removing the lower alcohol esters by at least one procedure chosen from deodorization, physical refining, evaporation and distillation, and
recovering the remaining fraction rich in triterpene esters.

2. The process according to claim 1, wherein the mixture comprises at least one vegetable oil chosen from rice bran oil, shea butter, shea butter oil, avocado oil, olive oil, soy bean oil, rape seed oil, mango butter, argan oil, palm oil, red palm oil, coconut oil, palm kernel oil, safflower oil, cocoa butter, almond oil, sun flower oil, peach kernel oil, evening primrose oil, sesame oil, illipe butter, borage oil, cotton seed oil, babassu oil, sal butter, kokum butter, corn oil, corn fiber oil, groundnut oil, flax seed oil, murumuru butter, cucpuacu butter and macadamia oil.

3. The process according to claim 1, wherein the mixture comprises at least one vegetable oil chosen from rice bran oil, shea butter, shea butter oil, and corn fiber oil.

4. The process according to claim 1, wherein the mixture is subjected to at least one procedure chosen from refining, degumming, neutralization, bleaching, deodorization, solvent fractionation, interesterification, partial hydrogenation and full hydrogenation before the mild transesterification.

5. The process according to claim 1, wherein the mild transesterification is performed with at least one lower alcohol chosen from ethanol and isopropanol.

6. The process according to claim 1, wherein the mild transesterification is performed with a mixture of methanol and ethanol.

7. The process according to claim 1, wherein the lower alcohol does not comprise more than 0.5 wt % water.

8. The process according to claim 1, wherein the mild transesterification is performed with at least one catalyst, wherein the catalyst is chosen from an acid catalyst and a base catalyst.

9. The process according to claim 1, wherein the mild transesterification is performed with an enzyme.

10. The process according to claim 1, wherein the mild transesterification is catalysed by at least one catalyst chosen from $NaOCH_3$, $NaOCH_2CH_3$, NaOH, and KOH.

11. The process according to claim 1, wherein the mild transesterification is performed at a temperature from 5° C. below the boiling point of the mixture to the boiling point of the mixture.

12. The process according to claim 1, wherein the mild transesterification is performed at a temperature not higher than 90° C.

13. The process according to claim 1, wherein the mild transesterification is performed at a temperature from about 60° C. to about 78° C.

14. The process according to claim 1, wherein the mild transesterification is performed during a reaction time from about 15 minutes to about 60 minutes.

15. The process according to claim 1, wherein a second mixture comprising at least one vegetable oil or a vegetable fat is added to the mixture after the mild transesterification and before the lower alcohol esters are removed.

16. A process for enriching triterpene esters comprising:
providing a first portion of a first mixture comprising at least one non-distilled vegetable oil or non-distilled vegetable fat, wherein the mixture further comprises at least one triterpene ester,
performing a mild transesterification with at least one lower alcohol at a temperature equal to or lower than the boiling point of the mixture to obtain lower alcohol esters,
providing a second portion of the first mixture,
removing the lower alcohol esters by at least one procedure chosen from deodorization, physical refining, evaporation and distillation, and
recovering the remaining fraction rich in triterpene esters,
wherein the second portion of the first mixture is added to the mixture after the mild transesterification and before the lower alcohol esters are removed.

17. The process according to claim 1, wherein the lower alcohol esters are removed at a temperature from 140° C. to 250° C.

18. The process according to claim 1, wherein the lower alcohol esters are removed at an increasing temperature starting from 140° C. to 190° C. and increasing the temperature to 200° C. to 250° C.

19. The process according to claim 1, wherein the lower alcohol esters are removed at a pressure from 1 mbar to 30 mbar.

20. The process according to claim 1, wherein the lower alcohol esters are removed with addition of steam.

21. The process according to claim 1, wherein the amount of triterpene esters in the remaining fraction is more than 85 wt %.

22. The process according to claim 1, wherein the peroxide value of the remaining fraction is less than 1 milliequivalents/kg.

23. The process according to claim 1, wherein the calculated weight ratio of triterpene esters to triterpenes alcohols in the remaining fraction is above 1.

24. The process according to claim 1, wherein the calculated weight ratio of triterpene esters to triterpenes alcohols in the remaining fraction is above 6.

25. A mixture comprising triterpene esters, wherein the mixture comprises more than 85 wt % triterpene esters, and wherein the amount of diglycerides in the mixture is less than 1 wt %.

26. The mixture according to claim 25, wherein the peroxide value of the mixture is less than 1 milliequivalents/kg.

27. The mixture according to claim 25, wherein the ratio of triterpene cinnamates to triterpene acetates in the mixture is from 1.5 to 3.

28. The mixture according to claim 25, wherein the calculated weight ratio of triterpene esters to triterpenes alcohols is above 1.

29. The mixture according to claim 25, wherein the calculated weight ratio of triterpene esters to triterpenes alcohols is above 6.

\* \* \* \* \*